(12) United States Patent
Smits et al.

(10) Patent No.: US 9,815,939 B2
(45) Date of Patent: Nov. 14, 2017

(54) POLYURETHANES

(71) Applicant: CRODA INTERNATIONAL PLC, Yorkshire (GB)

(72) Inventors: Angela Leonarda Maria Smits, Utrecht (NL); Karin Van Der Helm-Rademaker, Gouda (NL)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 14/422,554

(22) PCT Filed: Aug. 15, 2013

(86) PCT No.: PCT/GB2013/052177
§ 371 (c)(1),
(2) Date: Feb. 19, 2015

(87) PCT Pub. No.: WO2014/029975
PCT Pub. Date: Feb. 27, 2014

(65) Prior Publication Data
US 2015/0210807 A1      Jul. 30, 2015

(30) Foreign Application Priority Data

Aug. 23, 2012 (GB) .................................. 1214993.6

(51) Int. Cl.
| | |
|---|---|
| *C08G 18/42* | (2006.01) |
| *C09D 175/06* | (2006.01) |
| *C08G 71/04* | (2006.01) |
| *C08G 18/66* | (2006.01) |
| *C08G 18/76* | (2006.01) |
| *C08G 63/553* | (2006.01) |
| *C08G 18/08* | (2006.01) |
| *C08G 18/10* | (2006.01) |
| *C08G 18/75* | (2006.01) |
| *C07C 67/08* | (2006.01) |
| *C09J 175/06* | (2006.01) |

(52) U.S. Cl.
CPC .............. *C08G 71/04* (2013.01); *C07C 67/08* (2013.01); *C08G 18/0823* (2013.01); *C08G 18/0866* (2013.01); *C08G 18/10* (2013.01); *C08G 18/428* (2013.01); *C08G 18/4233* (2013.01); *C08G 18/4238* (2013.01); *C08G 18/4244* (2013.01); *C08G 18/4288* (2013.01); *C08G 18/6659* (2013.01); *C08G 18/755* (2013.01); *C08G 18/7671* (2013.01); *C08G 63/553* (2013.01); *C09D 175/06* (2013.01); *C09J 175/06* (2013.01)

(58) Field of Classification Search
CPC .............. C09D 175/06; C08G 18/4238; C08G 18/4244; C08G 18/428; C08G 18/4288; C08G 63/08; C08G 63/48; C08G 63/676
See application file for complete search history.

(56) References Cited

U.S. PATENT DOCUMENTS

| | | |
|---|---|---|
| 3,714,092 A | 1/1973 | Mazzeo |
| 4,101,422 A | 7/1978 | Lamont |
| 2001/0009956 A1 | 7/2001 | Gates |
| 2010/0016543 A1 | 1/2010 | Brenner |
| 2010/0112333 A1 * | 5/2010 | Cameron ............... C08G 18/10 428/315.5 |
| 2011/0135924 A1 | 6/2011 | Takahira |
| 2011/0207859 A1 | 8/2011 | Hasty |
| 2012/0125800 A1 | 5/2012 | Doreau |
| 2012/0208016 A1 | 8/2012 | Takahira |

FOREIGN PATENT DOCUMENTS

| | | | |
|---|---|---|---|
| EP | 0795572 | 9/1997 | |
| GB | 1027149 | 4/1966 | |
| JP | WO 2011049112 A1 * | 4/2011 | ............. B32B 27/00 |
| WO | 03070801 | 8/2003 | |
| WO | 2004056901 | 7/2004 | |

OTHER PUBLICATIONS

Pripol Polymerized Fatty Acids. www.croda.com 2008.*
International Preliminary Report on Patentability for International Application No. PCT/GB2013/052177 dated Feb. 24, 2015.
International Search Report for International Application No. PCT/GB2013/052177 dated Mar. 31, 2014.

* cited by examiner

*Primary Examiner* — Michael L Leonard
(74) *Attorney, Agent, or Firm* — RatnerPrestia

(57) ABSTRACT

The present invention relates to a polyurethane which is the reaction product of a polyisocyanate and polyester, wherein said polyester is formed from a dimer fatty acid, a $C_2$ to $C_4$ diol, and a $C_8$ to $C_{16}$ dicarboxylic acid or $C_6$ to $C_{12}$ lactide. The inventions also relates to a polyester for use in forming the polyurethane of the first aspect, said polyester formed from a dimer fatty acid, a $C_2$ to $C_4$ diol, and a $C_8$ to $C_{16}$ dicarboxylic acid or $C_6$ to $C_{12}$ lactide.

17 Claims, No Drawings

POLYURETHANES

CROSS REFERENCE TO RELATED APPLICATIONS

This application is the U.S. National Phase application of PCT International Application No. PCT/GB2013/052177, filed Aug. 15, 2013, and claims priority of Great Britain Application No. 1214993.6, filed Aug. 23, 2012, the disclosures of which are incorporated herein by reference in their entireties for all purposes.

FIELD OF INVENTION

The present invention relates to polyurethanes and polyurethane dispersions, a process of making the polyurethanes and dispersions thereof, and in particular to the use of said polyurethanes and polyurethane dispersions in coatings, adhesives, and elastomers compositions.

BACKGROUND

Polyurethanes are extremely versatile materials and have been used in a wide variety of applications such as foam insulation, car seats, paint coatings, and abrasion resistant coatings. Paint coating compositions are surface protective and/or decorative coatings which may be applied to substrates and allowed to dry or cure to form continuous protective and decorative films. Such coatings may be applied to a wide variety of substrates including metals, wood, plastics, and plaster. Important properties of the formed film include hardness and resistance to water.

Polyurethane dispersion polymers are an important class of binders for aqueous coating compositions, as they produce excellent properties, such as chemical and stain resistance, hardness and toughness in the solid coating.

Polyurethanes are also used in a wide variety of forms, for example non-cellular materials such as elastomers, and cellular materials such as low density flexible foams, high density flexible foams, and microcellular foams.

Polyurethanes, both in dispersion and non-dispersion forms, are also known to find use in adhesives, for example in deployment in the furniture industry.

EP0795572 is directed to the use of a polyester polyol, derived from terephthalic acid and adipic acid, to produce polyurethane foam for shoe soles.

WO 03/070801 describes microcellular polyurethane foams obtainable by reacting polyisocyanates with polyester, where the polyester is formed from a dimer fatty acid. In particular, this published document discloses use of dimer fatty acids of $C_{18}$ fatty acid monomer with adipic acid and diethylene glycol to form the polyester, and use of 4,4'-diphenylmethane diisocyanate as a polyisocyanate to form the polyurethane, WO 2004/056901 describes polyurethane based adhesives formed from polyisocyanates and polyols. In particular, this published document discloses use of dimer fatty acids of $C_{18}$ fatty acid monomer with adipic acid and ethylene or propylene glycol to form the polyester, and use of a mixture of 2,4'- and 4,4'-diphenylmethane diisocyanate as a polyisocyanate for forming the polyurethane, These known polyester based polyurethane compounds have a number of disadvantages, one being in relation to the sources of the individual building blocks. For example, the diol typically used in forming the polyester would be 1,6-hexanediol. However, this is prepared industrially by the hydrogenation of adipic acid. Production of (petrochemical-based) adipic acid and 1,6-hexanediol typically involves relatively large use of resources, and especially emission of nitrous oxide, resulting in a relatively large carbon footprint, which makes these components less environmentally friendly and therefore less desirable.

There is a growing need and desire to form polyesters and polyurethanes which can be synthesised from more renewable biobased components, and which have equivalent or improved physical properties in comparison to existing polyesters and polyurethanes as discussed herein.

SUMMARY OF THE INVENTION

The present invention therefore seeks to provide polyesters and polyurethanes made therefrom which may be formed from starting materials which may be biobased. In particular, the present invention seeks to provide polyesters and polyurethane which have mechanical and physical properties comparable to prior polyesters and polyurethanes. The present invention further seeks to provide a method of making the polyesters and polyurethanes.

The present invention also seeks to provide the use of polyurethanes or polyurethane dispersions in coating, adhesive, or elastomer compositions, and a coating, adhesive, or elastomer composition comprising said polyurethane or polyurethane dispersions.

According to a first aspect of the present invention there is provided polyurethane which is the reaction product of a polyisocyanate and polyester, wherein said polyester is formed from a dimer fatty acid, a $C_2$ to $C_4$ diol, and a $C_8$ to $C_{16}$ dicarboxylic acid or $C_6$ to $C_{12}$ lactide.

According to a second aspect of the present invention there is provided polyester for use in forming the polyurethane of the first aspect, said polyester formed from a dimer fatty acid, a $C_2$ to $C_4$ diol, and a $C_8$ to $C_{16}$ dicarboxylic acid or $C_6$ to $C_{12}$ lactide.

According to a third aspect there is provided a method of forming polyurethane of the first aspect, the method comprising;
   forming polyester from a dimer fatty acid, a polyol comprising $C_2$ to $C_4$ diol, and a $C_8$ to $C_{16}$ dicarboxylic acid or $C_6$ to $C_{12}$ lactide;
   reacting said polyester with a polyisocyanate to form polyurethane.

According to a fourth aspect there is provided a method of forming polyurethane of the first aspect, the method comprising;
   forming polyester from a dimer fatty acid, a polyol comprising $C_2$ to $C_4$ diol, and a $C_8$ to $C_{16}$ dicarboxylic acid or $C_6$ to $C_{12}$ lactide;
   reacting said polyester with polyisocyanate to form an isocyanate-terminated prepolymer; and
   reacting said prepolymer with a chain extender.

According to a fifth aspect of the present invention there is provided an isocyanate-terminated pre-polymer which is a reaction product of polyisocyanate and polyester, wherein said polyester is formed from a dimer fatty acid, a polyol comprising $C_2$ to $C_4$ diol, and a $C_8$ to $C_{16}$ dicarboxylic acid or $C_6$ to $C_{12}$ lactide.

According to a sixth aspect of the present invention there is provided the use of the polyurethane of the first aspect in an adhesive, coating, or elastomer composition.

According to a seventh aspect of the present invention there is provided an adhesive, coating, or elastomer composition comprising polyurethane of the first aspect.

DETAILED DESCRIPTION OF THE INVENTION

Surprisingly, it has been found that polyesters formed from a combination of a shorter chain diol with a longer chain dicarboxylic acid and dimer fatty acid provides for polyurethanes having comparable and, in some cases improved, physical properties. In particular, these physical properties may include hardness, scratch resistance, and moisture resistance when using the polyurethane in coatings, adhesives, or elastomers.

This is particularly unexpected as if the typically used diol 1,6 hexanediol is replaced with a shorter chain diol, it would be expected that decreased physical properties would normally be observed in the polyurethane comprising said polyester. These decreased properties may include inferior crystallinity and other properties of the polyurethane. However, it is surprisingly found that these detrimental effects can be countered by combining a shorter chain diol with dicarboxylic acid which has a chain length longer than typically used. The typically used dicarboxylic acid for forming polyester would be 1,6-adipic acid, and it has been found that this can be replaced with, for example, 1,12 dodecanedioic acid or 1,10-sebacic acid. This combination of shorter chain diol and longer chain dicarboxylic acid surprisingly provides polyesters and polyurethanes with properties comparable to, or in some cases better than, existing polyurethanes formed using 1,6 hexanediol.

As used herein, the terms 'for example,' for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branched groups.

Additionally, when describing the number of carbon atoms in, for example fatty acids, this refers to the total number of carbon atoms including the one at the carboxylic acid, and any present in any branch groups.

The term dimer fatty acid (also sometimes referred to as dimer fatty diacid) is well known in the art, and refers to the dimerisation products of mono- or polyunsaturated fatty acids and/or esters thereof. The related term trimer fatty acid similarly refers to trimerisation products of mono- or polyunsaturated fatty acids and/or esters thereof.

Dimer fatty acids are described T. E. Breuer, 'Dimer Acids', in J. I. Kroschwitz (ed.), Kirk-Othmer Encyclopedia of Chemical Technology, 4th Ed., Wily, New York, 1993, Vol. 8, pp. 223-237. They are prepared by polymerising fatty acids under pressure, and then removing most of the unreacted fatty acid starting materials by distillation. The final product usually contains some small amounts of mono fatty acid and trimer fatty acids, but is mostly made up of dimer fatty acids. The resultant product can be prepared with various proportions of the different fatty acids as desired.

The ratio of dimer fatty acids to trimer fatty acids can be varied, by modifying the processing conditions and/or the unsaturated fatty acid feedstock. The dimer fatty acid may be isolated in substantially pure form from the product mixture, using purification techniques known in the art, or alternatively a mixture of dimer fatty acid and trimer fatty acid may be employed.

The dimer fatty acids used in the present invention are preferably derived from the dimerisation products of $C_{10}$ to $C_{30}$ fatty acids, more preferably $C_{12}$ to $C_{24}$ fatty acids, particularly $C_{14}$ to $C_{22}$ fatty acids, further preferably $C_{16}$ to $C_{20}$ fatty acids, and especially $C_{18}$ fatty acids. Thus, the resulting dimer fatty acids preferably comprise in the range from 20 to 60, more preferably 24 to 48, particularly 28 to 44, further preferably 32 to 40, and especially 36 carbon atoms.

The fatty acids, from which the dimer fatty acids are derived, may be selected from linear or branched unsaturated fatty acids. The unsaturated fatty acids may be selected from fatty acids having either a cis/trans configuration, and may have one or more than one unsaturated double bonds.

Preferably, the fatty acids used are linear monounsaturated fatty acids.

Suitable dimer fatty acids are preferably derived from (i.e. are the dimer equivalents of) the dimerisation products of oleic acid, linoleic acid, linolenic acid, palmitoleic acid, or elaidic acid. In particular, suitable dimer fatty acids are derived from oleic acid.

The dimer fatty acids may be dimerisation products of unsaturated fatty acid mixtures obtained from the hydrolysis of natural fats and oils, e.g. sunflower oil, soybean oil, olive oil, rapeseed oil, cottonseed oil, or tall oil.

The molecular weight (weight average) of the dimer fatty acid is preferably in the range from 450 to 690, more preferably 500 to 640, particularly 530 to 610, and especially 550 to 590.

In addition to the dimer fatty acids, dimerisation usually results in varying amounts of trimer fatty acids (so-called "trimer"), oligomeric fatty acids, and residues of monomeric fatty acids (so-called "monomer"), or esters thereof, being present. The amount of monomer can, for example, be reduced by distillation.

Similarly, the optional trimer fatty acids are preferably derived from the trimerisation products of the materials mentioned with regard to the dimer fatty acids, and are preferably trimers of $C_{10}$ to $C_{30}$, more preferably $C_{12}$ to $C_{24}$, particularly $C_{14}$ to $C_{22}$, further preferably $C_{16}$ to $C_{20}$ fatty acids, and especially $C_{18}$ fatty acids. Thus, the trimer fatty acids preferably contain in the range from 30 to 90, more preferably 36 to 72, particularly 42 to 66, further preferably 48 to 60, and especially 54 carbon atoms.

The molecular weight (weight average) of the trimer fatty triacids is preferably in the range from 750 to 950, more preferably 790 to 910, particularly 810 to 890, and especially 830 to 870.

In one embodiment of the present invention, tetramer fatty acids and higher oligomers (hereinafter both referred to as oligomeric acids) are formed during production of the dimer fatty acid. Such oligomeric acids may therefore also be present in the dimer fatty acids used in the present invention, in combination with trimer fatty acids and/or dimer fatty acids and/or mono fatty monoacids.

The oligomeric acids are preferably oligomers, containing 4 or more units derived from $C_{10}$ to $C_{30}$, more preferably $C_{12}$ to $C_{24}$, particularly $C_{14}$ to $C_{22}$, and especially $C_{18}$ fatty acids. The molecular weight (weight average) of the oligomeric acid is suitably greater than 1,000, preferably in the range from 1,200 to 1,800, more preferably 1,300 to 1,700, particularly 1,400 to 1,600, and especially 1,400 to 1,550.

The dimer fatty acid used in the present invention preferably may have a dimer fatty acid (or dimer) content of greater than 60 wt. %, more preferably greater than 70 wt. %, particularly greater than 80 wt. %, and especially greater than 85 wt. %. Most preferably, the dimer content of the dimer fatty acid is in the range from 90 wt. % to 99 wt. %.

In an alternative embodiment, the dimer fatty acid preferably has a dimer fatty acid (or dimer) content in the range from 70 wt. % to 96 wt. %. This may be applicable in particular for two component or cross-linked systems.

In addition, particularly preferred dimer fatty acids may have a trimer fatty acid (or trimer) content of less than 40 wt. %, more preferably less than 30 wt. %, particularly less than 20 wt. %, and especially less than 15 wt. %. The trimer fatty acid content may be less than 1 wt. %.

Furthermore, the dimer fatty acid preferably comprises less than 10 wt. %, more preferably less than 6 wt. %, particularly less than 4 wt. %, and especially less than 3.5 wt. % of mono fatty monoacid (or monomer).

All of the above weight percentage values are based on the total weight of polymerised fatty acids and mono fatty acids present.

The polyol component used in forming the polyester of the present invention comprises a $C_2$ to $C_4$ diol. As used herein the term '$C_2$ to $C_4$ diol' refers to a 'lower alkyl' saturated hydrocarbon being straight chain or branched, containing 2 to 4 carbon atoms, and having two hydroxyl groups.

Suitable diols may be independently selected from straight chain aliphatic diols or branched aliphatic diols, or a combination thereof.

Suitable examples of straight chain aliphatic diols may be independently selected from ethylene glycol, diethylene glycol, 1,3-propylene glycol (better known as 1,3-propanediol), and 1,4-butanediol.

Suitable examples of branched aliphatic diols may be independently selected from 1,2-propylene glycol, 1,2-butanediol, 2,3-butanediol, and 1,3-butanediol.

Preferably, said $C_2$ to $C_4$ diol is selected from a straight chain aliphatic diol. More preferably, said diol is selected from 1,3-propylene glycol (better known as 1,3-propanediol), 1,4-butanediol, or a combination thereof. Most preferably, said diol is 1,3-propylene glycol or 1,4-butanediol.

The $C_2$ to $C_4$ diol component of the polyester used in the present invention suitably has a molecular weight in the range from 60 to 120, preferably 70 to 100, more preferably 75 to 95.

Said polyol component, used to form the polyester of the present invention, preferably comprises at least 50 wt. % of $C_2$ to $C_4$ diol. More preferably, said polyol comprises at least 65 wt. % of $C_2$ to $C_4$ diol. Further preferably, said polyol comprises at least 75 wt. % of $C_2$ to $C_4$ diol. Particularly preferably, said polyol comprises at least 85 wt. % of $C_2$ to $C_4$ diol. In particular, said polyol comprises at least 90 wt. % of $C_2$ to $C_4$ diol. Most preferably, said polyol comprises at least 98 wt. % of a $C_2$ to $C_4$ diol. The weight percentages are expressed as a proportion of the total polyol content.

The $C_2$ to $C_4$ diol is preferably derived from renewable and/or bio-based sources. The level of this may be determinable by ASTM D6866 as a standardised analytical method for determining the bio-based content of samples using $^{14}C$ radiocarbon dating. ASTM D6866 distinguishes carbon resulting from bio-based inputs from those derived from fossil-based inputs. Using this standard, a percentage of carbon from renewable sources can be calculated from the total carbon in the sample.

Preferably, the $C_2$ to $C_4$ diol has a renewable carbon content of at least 50% when determined using ASTM D6866. More preferably, at least 65%. Most preferably, at least 80%.

The polyol component may comprise polyols which are not $C_2$ to $C_4$ diols. Suitable polyols may be selected from diols of $C_5$ or greater, or from polyols having a hydroxyl function greater than 2.

Suitable examples of $C_5$ or greater diols may be independently selected from dipropylene glycol, 1,5-pentanediol, 1,8-octanediol, 1,6-hexanediol, 1,7-heptanediol, 1,2-pentanediol, etohexadiol, neopentyl glycol, 4-bis(hydroxymethyl)cyclohexane, (1,4-cyclohexane-dimethanol), polyesters (for example adipate esters), and polyethers (for example polytetramethylene ether glycol (PTMEG) or poly(propylene glycol) (PPG)).

Suitable polyols having a hydroxyl function greater than 2 may include glycerol, pentaerythritol, or trimethylolpropane.

The polyol component may also comprise a dimer fatty diol. Dimer fatty acids are discussed herein, and dimer fatty diols may be formed by hydrogenation of the corresponding dimer fatty acid. The same preferences detailed for the dimer fatty acid apply to the corresponding dimer fatty diol component of the polyester.

The polyester is also formed from a $C_8$ to $C_{16}$ dicarboxylic acid component, and this will be understood to be a non-dimeric dicarboxylic acid (also referred to as non-dimeric acid) and distinct from the dimer fatty acids described herein.

The non-dimeric acids may be aliphatic or aromatic. Said acids may include dicarboxylic acids and the esters thereof, preferably alkyl esters and more preferably dimethyl esters.

Said acids may be linear dicarboxylic acids, in that they comprise terminal carboxyl groups, wherein the terminal carboxyl groups are bridged by a $C_6$ to $C_{14}$ alkyl group, or a $C_6$ to $C_{14}$ alkenyl group.

The term '$C_6$ to $C_{14}$ alkyl' as used herein, unless otherwise defined, refers to saturated hydrocarbon radicals being straight chain, branched, or cyclic moieties, containing from 6 to 14 carbon atoms.

The term '$C_6$ to $C_{14}$ alkenyl' as used herein, unless otherwise defined, refers to hydrocarbon radicals having in the range from 6 to 14 carbon atoms, and comprising at least one carbon-carbon double bonds. The alkenyl radicals may be straight chain or branched. Preferably, the non-dimeric acid is linear and has a $C_6$ to $C_{14}$ alkyl bridging group.

In one embodiment, said non-dimeric acid may be selected from a linear aliphatic dicarboxylic acid comprising in the range from 8 to 16 carbon atoms. Preferably, in the range from 10 to 14 carbon atoms. Most preferably, in the range from 10 to 12 carbon atoms.

In this embodiment, preferred examples of non-dimeric acids may be independently selected from suberic acid, azelaic acid, sebacic acid (decanedioic acid), undecane dicarboxylic acid, dodecane dicarboxylic acid (dodecanedioic acid), or combinations thereof. More preferably, said acid is selected from sebacic acid or dodecanedioic acid.

Alternatively, said acids may comprise terminal carboxyl groups bridged by at least one cyclic group. The cyclic groups may be saturated or unsaturated cyclic groups, and may be selected from 4 to 7 membered rings. Preferably the or each cyclic group is selected from $C_5$ or $C_6$ cycloalkyls or $C_6$ cycloaryl.

The term 'cycloalkyl' as used herein, unless otherwise defined, refers to an organic radical derived from a saturated hydrocarbon, and may be selected from cyclopentane or cyclohexane. The term 'cycloaryl' as used herein, unless otherwise defined, refers to an organic radical derived from an aromatic hydrocarbon by removal of one hydrogen, and may be phenyl.

In the embodiment where the terminal carboxyl groups are bridged by at least one cyclic group, suitable examples of non-dimeric acids may be selected from terephthalic acid, (ortho) phthalic acid or isophthalic acid.

Preferably, said non-dimeric acid is selected from aliphatic non-dimeric acids. More preferably, said acid is selected from sebacic acid, 1,12 dodecanedioic acid, or terephthalic acid, or a combination thereof.

The non-dimeric acid is preferably derived from renewable and/or biobased sources. The level of this may be determinable by ASTM D6866 as described herein. Preferably, the non-dimeric acid has a renewable carbon content of at least 50% when determined using ASTM D6866. More preferably, at least 65%. Further preferably, at least 80%. Most preferably, a renewable carbon content of greater than 95%.

Said non-dimeric acid component used to form the polyester of the present invention preferably comprises at least 50 wt. % of a $C_8$ to $C_{16}$ dicarboxylic acid. More preferably, said non-dimeric acid comprises at least 65 wt. % of a $C_8$ to $C_{16}$ acid. Further preferably, said non-dimeric acid comprises at least 75 wt. % of a $C_8$ to $C_{16}$ acid. Particularly preferably, said non-dimeric acid comprises at least 85 wt. % of a $C_8$ to $C_{16}$ acid. More preferably, at least 90% wt. %, most preferably at least 98 wt. %.

The non-dimeric acid component may comprise acids which are not $C_8$ to $C_{16}$ dicarboxylic acids. Suitable acids may be selected from adipic acid, glutaric acid, succinic acid, pimelic acid, or heptane dicarboxylic acid.

A monomeric dicarboxylic acid anhydride, such as phthalic anhydride, may also be employed as the or as part of the non-dimeric acid component.

The $C_6$ to $C_{12}$ lactide may be any suitable substituted or unsubstituted lactide. Lactide will be understood to refer to the cyclic di-ester of lactic acid. The lactide may be substituted with one or more $C_1$ to $C_6$ alkyl groups. Said alkyl groups may be independently selected from methyl, ethyl, n-propyl, isopropyl, n-butyl, isobutyl, sec-butyl, tert-butyl, 2 methyl-butyl, pentyl, hexyl, cyclohexyl, or the like.

Preferably, the lactide is an unsubstituted lactide.

The lactide is preferably derived from renewable and/or biobased sources. The level of this may be determinable by ASTM D6866 as described herein. Preferably, the lactide has a renewable carbon content of at least 50% when determined using ASTM D6866. More preferably, at least 65%. Further preferably, at least 80%. Most preferably, a renewable carbon content of greater than 95%.

The polyester used in the present invention is formed from, i.e. comprises the reaction product of, at least one dimer fatty acid and/or equivalent thereof, $C_2$ to $C_4$ diol, and $C_8$ to $C_{16}$ dicarboxylic acid or $C_6$ to $C_{12}$ lactide. The polyester may be formed by a condensation reaction.

The ratio of the number of carbon atoms in the $C_2$ to $C_4$ diol to the ratio of carbon atoms in the dicarboxylic acid or lactide component is preferably in the range from 1:1.5 to 12 respectively. Preferably, in the range from 1:2 to 8. More preferably, in the range from 1:3 to 6. Most preferably, in the range from 1:3.5 to 5.

The polyester is preferably formed with dimer fatty acids to non-dimer acids present at a ratio in the range from 10 to 100:0 to 90, more preferably 30 to 70:30 to 70, particularly 40 to 60:40 to 60.

The polyester is preferably formed from dicarboxylic acid to diol starting materials at a molar ratio in the range from 1:1.0 to 5.0, more preferably 1:1.05 to 3.0, particularly 1:1.1 to 2.0, and especially 1:1.2 to 1.4. Thus, the diol is preferably present in molar excess so as to obtain polyester terminated at both ends with hydroxyl groups.

In a preferred embodiment, the polyester is formed from dimer fatty acid; $C_{10}$ or $C_{12}$ dicarboxylic acids; and 1,3 propanediol or 1,4 butane diol; preferably at a weight ratio in the range from 0.3 to 0.7:0.3 to 0.7:1.0 to 3.0, more preferably 0.4 to 0.6:0.4 to 0.6:1.1 to 2.0, particularly 0.45 to 0.55:0.45 to 0.55:1.2 to 1.4, and especially 0.5:0.5:1.3.

The polyester preferably has a molecular weight number average in the range from 800 to 5,000, more preferably 1,700 to 3,000 or 2,500-4,000, particularly 1,800 to 2,500 or 2,600-3,500, and especially 1,900 to 2,200 or 2,800-3,100.

The polyester preferably has a glass transition temperature ($T_g$) value (measured as described herein) in the range from −60° C. to 0° C., more preferably −50° C. to −5° C., particularly −40 to −10° C.

The polyester preferably has a hydroxyl value (measured as described herein) in the range from 10 to 100, more preferably 30 to 80, particularly 30 to 70, and especially 33 to 60 mgKOH/g.

In addition, the polyester preferably has an acid value (measured as described herein) of less than 2, more preferably less than 1.7, particularly less than 1.3, and especially less than 1.0.

In one embodiment of the invention, non-dimer (acid or diol) containing polyester, may also be employed in forming the polyurethane, in addition to the dimer fatty (acid and/or diol) containing polyesters described herein. Suitable non-dimer containing materials include polyesters derived from diols such as ethylene glycol, diethylene glycol, 1,4-butylene glycol, or speciality glycols and other special components, e.g. caprolactone.

When the optional non-dimer containing polyester is present, the polyurethane is formed from dimer-containing polyester to non-dimer containing polyester (both in the form of polyester and/or in an isocyanate-terminated prepolymer form) preferably at a ratio in the range from 10 to 95:5 to 90, more preferably 30 to 90:10 to 70, particularly 40 to 80:20 to 60, and especially 50 to 70:30 to 50% by weight.

The polyisocyanate component is preferably at least one isocyanate which has a functionality of at least 2, and may be an aliphatic isocyanate, such as hexamethylene 1,6-diisocyanate or isophorone diisocyanate (IPDI). Alternatively, the polyisocyanate is an aromatic isocyanate. Preferably, the polyisocyanate is an aliphatic isocyanate.

Suitable aromatic isocyanates may be selected from tolylene diisocyanate, m-phenylene diisocyanate, p-phenylene diisocyanate, xylylene diisocyanate, 4,4'-diphenylmethane diisocyanate, hexamethylene diisocyanate, isophorone diisocyanate, polymethylenepolyphenyl diisocyanate, 3,3'-dimethyl-4,4'-biphenylene diisocyanate, 3,3'-dimethyl-4,4'-diphenylmethane diisocyanate, 3,3-dichloro-4,4'-biphenylene diisocyanate, 1,5-naphthalene diisocyanate, or modified compounds thereof such as uretonimine-modified compounds thereof.

The polyisocyanate monomers can be used alone or as mixtures thereof. In a preferred embodiment, 4,4'-diphenylmethane diisocyanate (MDI) is used alone, or more preferably a mixture of MDI and a uretonimine-modified 4,4'-diphenylmethane diisocyanate (modified MDI) is employed. Alternatively, isophorone diisocyanate (IPDI) may preferably be used, especially for forming polyurethanes to be used in coatings or adhesives.

The method of forming polyurethane may optionally include the step of forming a prepolymer by reacting the polyester with a polyisocyanate to form an isocyanate-terminated prepolymer, and forming polyurethane from said prepolymer, optionally in the presence of a chain extender.

The prepolymer reaction mixture may preferably have an isocyanate content (measured as described herein) in the range from 5% to 30%, more preferably 15 to 23%, particularly 17% to 20%, and especially 18% to 19% NCO.

In one embodiment of the invention, at least one of the aforementioned polyisocyanates is reacted with at least one of the aforementioned polyesters, to form said prepolymer.

The ratio of polyisocyanate to polyester starting materials which are mixed together to react to form the prepolymer is preferably in the range from 20 to 80:20 to 80, more preferably 35 to 75:25 to 65, particularly 45 to 70:30 to 55, and especially 55 to 65:35 to 45 by weight.

The polyisocyanate is preferably used in molar excess relative to hydroxyl group content of the polyester, so as to obtain a reaction mixture containing isocyanate-terminated prepolymer and sufficient unreacted polyisocyanate, such that later addition of the chain extender can result in reaction to form the polyurethane foam, without the requirement for adding further polyisocyanate.

The polyurethane according to the present invention may be produced by efficiently mixing the polyester with polyisocyanate.

In the polyurethane synthesis, the NCO/OH ratio employed is preferably in the range from 1 to 1.2:1, more preferably 1 to 1.1:1., and particularly 1 to 1.03:1.

Alternatively, the polyurethane may be formed by mixing prepolymer, formed as described herein, with polyisocyanate, optionally in the presence of chain extenders.

The polyester and polyisocyanate may be reacted at an elevated temperature. Said elevated temperature may be in the range from 50° C. to 80° C. Preferably, in the range from 60° C. to 75° C.

A chain extender may optionally be present for the method of forming polyurethane. The chain extender may be in the form of a chain extender composition. The chain extender composition is preferably prepared by simple premixing of, for example, the chain extender, polyester and other additives (such as blowing agent, and/or urethane catalyst, and/or pigment and/or filler and/or blowing agent). At least one of the aforementioned polyesters may be added together with the chain extender to react with a prepolymer in order to form the polyurethane.

The chain extender component used to form the polyurethane suitably comprises a low molecular compound having two or more active hydrogen groups, for example polyols such as ethylene glycol, diethylene glycol, propylene glycol, 1,4-butylene glycol, 1,5-pentylene glycol, methylpentanediol, isosorbide (and other iso-hexides), 1,6-hexylene glycol, neopentyl glycol, trimethylolpropane, hydroquinone ether alkoxylate, resorcinol ether alkoxylate, glycerol, pentaerythritol, diglycerol, and dextrose; dimer fatty diol; aliphatic polyhydric amines such as ethylenediamine, hexamethylenediamine, and isophorone diamine; aromatic polyhydric amines such as methylene-bis(2-chloroaniline), methylenebis(dipropylaniline), diethyl-toluenediamine, trimethylene glycol di-p-aminobenzoate; alkanolamines such as diethanolamine, triethanolamine and diisopropanolamine.

In a preferred embodiment of the invention, the chain extender is a polyol, more preferably a diol, particularly having an aliphatic linear carbon chain comprising in the range from 1 to 10, and especially 3 to 5 carbon atoms. Preferred diols include ethylene glycol, propylene glycol, 1,4-butylene glycol, and 1,5-pentylene glycol. 1,4-butylene glycol is particularly preferred.

The molar ratio of chain extender to polyester employed is preferably in the range from 1 to 10:1, more preferably 1.5 to 8:1, particularly 2 to 5:1, and especially 2.5 to 4:1. The polyester employed may be the same as or different to the polyester used to form the prepolymer.

In the present invention, the chain extender composition may optionally contain other additives such as blowing agents, urethane promoting catalysts, pigments, fillers, blowing agents, surfactant, and stabilisers.

Suitable blowing agents include water, and fluorocarbons such as trichlorofluoromethane, dichlorodifluoromethane and trichlorodifluoroethane. The blowing agents may be used alone or as mixtures thereof.

Examples of urethane catalysts include tertiary amines such as triethylamine, 1,4-diazabicyclo[2.2.2.]octane (DABCO), N-methylmorpholine, N-ethylmorpholine, N,N, N',N'-tetramethylhexamethylenediamine, 1,2-dimethylimidazol; and tin compounds such as tin(II)acetate, tin(II) octanoate, tin(II)laurate, dibutyltin dilaurate, dibutyltin dimaleate, dioctyltin diacetate and dibutyltin dichloride. The catalysts may be used alone or as mixtures thereof.

Suitable surfactants include silicone surfactants such as dimethylpolysiloxane, polyoxyalkylene polyol-modified dimethylpolysiloxane and alkylene glycol-modified dimethylpolysiloxane; and anionic surfactants such as fatty acid salts, sulphuric acid ester salts, phosphoric acid ester salts and sulphonates.

Examples of the stabilisers include hindered phenol radical scavengers such as dibutylhydroxytoluene, pentaerythrityl-tetrakis[3-(3,5-di-t-butyl-4-hydroxyphenyl)propionate] and isooctyl-3-(3,5-di-t-butyl-4-hydroxyphenyl)propionate; antioxidants such as phosphorous acid compounds such as triphenylphosphite, triethylphosphite and triphenylphosphine; ultraviolet absorbing agents such as 2-(5-methyl-2-hydroxyphenyl)benzotriazole and a condensation product of methyl-3-[3-t-butyl-5-(2H-benzotriazole-2-yl)-4-hydroxyphenyl]propionate and polyethylene glycol.

Suitable pigments include inorganic pigments such as transition metal salts; organic pigments such as azo compounds; and carbon powder. Suitable fillers include inorganic fillers such as clay, chalk, and silica.

The dimer fatty acid content of the formed polyurethane is preferably in the range from 5 to 50%, more preferably 8 to 40%, particularly 12 to 30%, and especially 15 to 20% by weight.

The formed polyurethane is preferably derived from renewable and/or bio-based sources. The level of this may be determinable by ASTM D6866 as described herein.

Preferably, the polyurethane has a renewable carbon content of at least 50% when determined using ASTM D6866. More preferably, at least 65%. Most preferably, at least 80%.

It has been found that use of existing polyesters may make the polyurethane susceptible to hydrolysis, or degradation by UV/thermo-oxidation. These shortcomings limit the application possibilities of conventional polyurethanes. Polyurethanes formed using polyesters of the present invention are found to provide polyurethanes with good thermo-oxidative and UV stability. Additionally, said polyurethanes may have good thermal stability, and good hydrolytic stability thereby offering resistance against attack by acids, alkali, and alcohol.

The polyurethanes may be formed in to a dispersion, in particular if they are to be used in coating compositions or adhesive compositions. Said dispersions may comprise in the range from 10 wt. % to 80 wt. % polyurethane. Preferably, from 20 wt. % to 60 wt. % polyurethane. More preferably, from 30 wt. % to 50 wt. % polyurethane.

The polyurethane may be used in many applications. The polyurethane of the present invention may be used in coating compositions, adhesive compositions, or elastomers. In particular, the polyurethane may find application in coating compositions, for example in protective coatings.

Protective or decorative coatings prepared from a composition according to the present invention can be formulated with a wide variety of ingredients well known to those skilled in the art of coating formulation, including solvents, fillers, pigments, pigment dispersing agents, rheology modifiers, thixotropes, flow and leveling aids, defoamers, etc.

Coating compositions of the present invention can be applied by any number of techniques including spray, brush, roller, paint mitt, and the like. Numerous substrates are suitable for application of coatings of this invention with proper surface preparation, as is well understood in the art. Such substrates include, but are not limited to, many types of metal, particularly steel and aluminium, as well as concrete.

The coating compositions may be suitable for use as a primer coating on substrates such as concrete and steel. A preferred coating or overcoat layer to be used on top of a primer coating layer. Coatings of this invention can be applied and cured at ambient temperatures ranging from about 0° C. to about 50° C.

The coatings compositions comprising polyurethanes of the present invention may have a number of desired properties.

The modulus will be understood to represent the force (stress) required to produce a certain elongation (strain) in this case 100%, i.e. a measure of tensile strength at a 100% elongation. Compounds with a higher modulus will be understood to be more resilient and more resistant to extrusion.

The coating compositions may have a 100% modulus value of greater than 12 $kg/cm^2$. Preferably, the coating compositions may have a 100% modulus value in the range from 15 to 40 $kg/cm^2$. More preferably, in the range from 17 to 32 $kg/cm^2$. Most preferably, in the range from 20 to 28.

A particular advantage of the polyurethane according to the present invention is that it is resistant absorption of water, and has low moisture uptake/low moisture absorption. The coating composition comprising polyurethane may absorb less than 10% water after 24 hours. More preferably, less than 8%.

The coating hardness is the resistance of a coating to a mechanical force such as pressure, rubbing, or scratching. The hardness of the coating composition comprising polyurethane is indicated by the König hardness. The coating hardness is preferably greater than 22 König hardness units, more preferably greater than 24 König hardness units, and most preferably greater than 26 König hardness units.

The polyurethane may also be used in adhesive compositions. The adhesive may preferably be applicable to a suitable substrate, preferably wood, in situ as a free flowing viscous solid, and cured, by reacting with water present in the substrate, at ambient temperature. Adhesives based on polyurethane of the present invention are for example, used for the lamination of furniture front panels and automotive interior trim parts, and for the bonding of shoe soles. In these applications, strong and reliable initial bond strength is essential as the finished parts are often processed further immediately after the bonding process and short cycle times are fundamental.

The adhesive preferably has a viscosity at 23° C. in the range from 2 to 40, more preferably 3 to 30, particularly 4 to 20, and especially 5 to 10 Pa·s.

The adhesive may also comprise other optional components such as fillers, for example nylon, glass fibre, fumed silica, wood flour; and other agents such as pigments, antioxidants, stabilizers, flow additives etc.

The polyurethane may also be used in elastomer compositions. These elastomer compositions may be solid elastomers or microcellular elastomers.

The elastomer compositions may have a 100% modulus value of greater than 40 $kg/cm^2$. Preferably, the elastomer composition may have a 100% modulus value in the range from 50 to 90 $kg/cm^2$. More preferably, in the range from 60 to 80 $kg/cm^2$.

The elastomers compositions comprising polyurethane of the present invention may also exhibit good hardness properties. The hardness of the elastomer may be defined as the material's resistance to permanent indentation.

The elastomer composition preferably have a hardness in the range from 40 to 110, more preferably 60 to 100, particularly 70 to 90 Shore A.

All of the features described herein may be combined with any of the above aspects, in any combination.

EXAMPLES

In order that the present invention may be more readily understood, reference will now be made, by way of example, to the following description.

It will be understood that all tests and physical properties listed have been determined at atmospheric pressure and room temperature (i.e. 25° C.) unless otherwise stated herein, or unless otherwise stated in the referenced test methods and procedures. Tests of polyurethane dispersions in coatings were performed at 23° C. with a relative humidity of 50%.

Compounds as used in the following examples are identified as follows:

1,3-propanediol—bio-based Susterra propanediol obtained from DuPont Tate & Lyle
1,4-butanediol—bio-based obtained from BioAmber
1,6-hexanediol
Succinic acid, ($C_4$ dicarboxylic acid)—bio-based obtained from Reverdia or Myriant technologies
Adipic acid ($C_6$ dicarboxylic acid)—bio-based obtained from Verdezyne
Suberic acid ($C_8$ dicarboxylic acid)
Azelaic acid ($C_9$ dicarboxylic acid)—bio-based
Sebacid acid ($C_{10}$ dicarboxylic acid)—bio-based
Undecanedioic acid ($C_{11}$ dicarboxylic acid)
Dodecanedioic acid ($C_{12}$ dicarboxylic acid)—bio-based obtained from Cathay Biotechnology
Phthalic acid (anhydride)
Dimer acid hydrogenated, $C_{36}$ dicarboxylic acid Test Methods:

The glass transition temperature ($T_g$) was measured by Differential Scanning Calorimetry (DSC) at a scan rate of 20° C./minute using a Mettler DSC30.
Molecular weight number average was determined by end group analysis.
The hydroxyl value is defined as the number of mg of potassium hydroxide equivalent to the hydroxyl content of 1 g of sample, and was measured by acetylation followed by hydrolysation of excess acetic anhydride. The acetic acid formed was subsequently titrated with an ethanolic potassium hydroxide solution.
The acid value is defined as the number of mg of potassium hydroxide required to neutralise the free fatty acids in 1 g of sample, and was measured by direct titration with a standard potassium hydroxide solution. The isocyanate value is defined as the weight % content of isocyanate in the sample and was determined by reacting with excess dibutylamine, and back titrating with hydrochloric acid.

Hardness was measured using a Shore A meter on a 10 mm thick sample. Mean value of 10 readings calculated.

Impact resilience was measured according to ASTM D3574 (falling ball rebound test).

Hydrolysis Samples were aged by placing dumbbells of the material in a climate chamber at 70 C and >98% relative humidity for periods of 2 and 4 weeks. The tensile strength and elongation at break of the "aged" samples were determined as above and the values compared to the original figures (on percentage retention terms).

Examples 1-5

Formation of Polyesters with Various Dicarboxylic Acids

Polyesters were formed using a variety of diols and dicarboxylic acids of differing chain lengths. Dimer fatty diacid derived from $C_{18}$ fatty acids was used in each example. The dicarboxylic acid component was varied by chain length, using $C_4$ and $C_6$ dicarboxylic acids (for comparison), and $C_{10}$ and $C_{12}$ dicarboxylic acids.

The dimer fatty acid and dicarboxylic acid were present at a ratio of 50:50 by weight percent.

All the polyesters in Examples 1 to 5 were made at molecular weight 2,000 with hydroxyl values of 56 mgKOH/g.

Example 1—1,6-hexanediol, $C_{36}$ dimer fatty diacid, adipic acid

Example 2—1,3-propanediol, $C_{36}$ dimer fatty diacid, succinic acid

Example 3—1,3-propanediol, $C_{36}$ dimer fatty diacid, adipic acid

Example 4—1,3-propanediol, $C_{36}$ dimer fatty diacid, sebacic acid

Example 5—1,3-propanediol, $C_{36}$ dimer fatty diacid, dodecanedioic acid

Examples 1 to 3 were made for comparative purposes. These comparative examples do not fall with the scope of this invention.

Examples 6-9

Polyesters Made With Dimer Fatty Acid and 1,12-Dodecanedioic Acid at Various Ratios Four samples of polyester were made from 1,3-propanediol, dimer fatty diacid, and 1,12-dodecanedioic acid. The dimer fatty diacid was derived from $C_{18}$ fatty acids. The ratio of dimer fatty diacid and 1,12-dodecanedioic acid was varied in the examples.

All the polyesters in Examples 6 to 10 were made at molecular weight 2,000 with hydroxyl values of 56 mgKOH/g.

Example 6—dimer fatty diacid 75:25 1,12-dodecanedioic
Example 7—dimer fatty diacid 50:50 1,12-dodecanedioic
Example 8—dimer fatty diacid 40:60 1,12-dodecanedioic
Example 9—dimer fatty diacid 25:75 1,12-dodecanedioic Examples 10-13

Formation of Polyesters with Butanediol

Examples 10 to 13 are equivalent to Examples 1 and 3 to 5 and were made in the same way, except propanediol in Examples 3 to 5 was replaced with butanediol in Examples 11 to 13.

Example 10—1,6-hexanediol, C36 dimer fatty acid, adipic acid (comparative)

Example 11—1,4-butanediol, C36 dimer fatty acid, adipic acid (comparative)

Example 12—1,4-butanediol, C36 dimer fatty acid, sebacic acid

Example 13—1,4-butanediol, C36 dimer fatty acid, dodecanedioic acid

Examples 10 and 11 were made for comparative purposes. These comparative examples do not fall within the scope of the invention.

Example 14-15

Polyesters Made with Dimer Fatty Acid an 1,12-Dodecanedioic Acid at Various Ratios Examples 14 and 15 are equivalent to Examples 6 and 7 and were made in the same way, except propanediol in Examples 6 and 7 was replaced with butanediol in Examples 14 and 15.

Polyesters made from 1,4-butanediol, C36 dimer fatty acid, dodecanedioic acid at OH value 56 mgKOH/g.

Example 14—1,4- butanediol, dimer fatty acid 75:25 1,12-dodecanedioic acid

Example 15—1,4- butanediol, dimer fatty acid 50:50 1,12-dodecanedioic acid

Examples D1-D15

Polyurethane Dispersions used in Coatings

Polyurethane dispersions were made from the polyesters of Examples 1 to 5, with each dispersion labelled D1 to D5 respectively. The polyurethane dispersions of Examples D1 to D5 were synthesised via formation of a pre-polymer, and the components present are shown in Table 1.

TABLE 1

| Components for D1 to D5 Synthesis | | |
|---|---|---|
| Amount Used | Component | Function |
| 60.75 g | Polyester | |
| 5.1 g | 2,2-Dimethoxy-2-phenylacetophenone (DMPA) | |
| 22.9 g | Isophorone diisocyanate (IPDI) | Polyisocyanate |
| 11.2 g | N-Methyl-2-pyrrolidone (NMP) | Organic solvent |
| 1.1 g | Ethylenediamine (EDA) | |
| 150 g | Water | |

The polyester, DMPA and NMP were dried at 120° C. under nitrogen. After cooling to 70° C., dibutyl tin dilaurate (DBTL) catalyst (0.05 wt. % based on the weight of the pre-polymer) and IPDI were slowly added over approximately 3 hours to produce the pre-polymer. Then at 60° C. triethylamine was added to neutralise the DMPA carboxylic acid groups over a period of 0.5 to 1 hour. The reaction mixture was then cooled to 40-55° C. After cooling, the prepolymer was dispersed in demineralised water which was added slowly over 1 hour under vigorous stirring.

Once the reaction mixture had reached 25° C., EDA was added in order to chain extend the prepolymer. EDA was added drop-wise and reacted over two hours. The resultant dispersion comprised 40 wt. % of the polyurethane. Acetone was used as processing aid to reduce viscosity, and was then be distilled off from the final polyurethane dispersion.

This was repeated for each of Examples 1 to 5 to yield polyurethane dispersions D1 to D5. Various physical properties were measured for each dispersion in the form of a coating.

The following methods were used to provide measurement of the listed parameters as shown in Table 2.
Particle size—Zetasizer using dynamic light scattering
Modulus—tensile test on polyurethane dispersion as a thick dried film
König hardness—tested using DIN ISO 2815
Impact strength—tested using DIN ISO 6272
Chemical resistance—Spot test, where rating were assigned of 0=undamaged to 5=complete damage
Water absorption—determined by measuring weight increase after 24h in demi-water at room temperature.

TABLE 2

Evaluation of coatings comprising polyurethane dispersions of D1 to D5

|  | D1 | D2 | D3 | D4 | D5 |
|---|---|---|---|---|---|
| Particle size (nm) | 75 | 47 | 56 | 78 | 103 |
| 100% modulus (kg/cm$^2$) | 21 | 8 | 23 | 22 | 27 |
| König hardness (s) | 29 | 20 | 27 | 31 | 41 |
| Impact direct/indirect (kgcm) | 200/200 | 200/200 | 200/200 | 200/200 | 200/200 |
| Water absorption (%) | 6 | Dissolved | 7 | 6 | 6 |
| Chemical resistance to: | | | | | |
| NH$_3$ (10%, 2 min) | 0 | 5 | 2 | 0 | 0 |
| NaCl (5%, 5 hour) | 1 | 5 | 1-2 | 0 | 0 |
| Water (16 hour) | 1 | 5 | 5 | 4 | 2 |
| Acetone (10%, 10 h) | 4 | 4 | 4 | 4 | 3 |

Examples D1 to D5 show that, upon increasing the molecular weight of the dicarboxylic acid, increases were seen in both the modulus and hardness of the polyurethane. Also an increase was also observed in the chemical resistance to ammonia, salt, and water. Impact resistance was found to be good for all polyurethane dispersions.

The comparative example D1 based on 1,6-hexanediol instead of 1,3-propanediol, resulted in similar modulus and higher hardness than with 1,3-propanediol with dimer fatty acid and adipic acid (at 50:50 ratio)—as shown in comparative Examples D2 and D3. However, results were further improved when 1,3-propanediol was combined with longer chain dicarboxylic acids such as decanedioic or dodecanedioic acids—as shown in Examples D4 and D5. Replacement of 1,6-hexanediol by 1,3-propanediol alone results in reduced chemical resistance. However, this also improved when combined with longer chain dicarboxylic acids.

Polyurethane dispersions were also formed from the polyurethanes of Examples 6 to 9 using the same method as described for Examples D1 to D5. Dispersions D6 to D9 were formed, and various physical properties were measured for each dispersion in the form of a coating.

The test methods used to determine the properties as shown in Table 3 were the same as described with reference to dispersions D1 to D5.

TABLE 3

Evaluation of coatings comprising polyurethane dispersions of D6 to D9

|  | D6 | D7 | D8 | D9 |
|---|---|---|---|---|
| Particle size (nm) | 165 | 103 | 110 | 82 |
| 100% modulus (kg/cm) | 30 | 27 | 36 | 42 |
| König hardness (s) | 43 | 41 | 38 | 36 |
| Impact direct/indirect (kgcm) | 200/200 | 200/200 | 200/200 | 200/200 |
| Water absorption (%) | 46 | 8 | 7 | 20 |
| Chemical resistance to: | | | | |
| NH$_3$ (10%, 2 min) | 0 | 0 | 0 | 0 |
| NaCl (5%, 5 hour) | 0 | 0 | 0-1 | 1 |
| Water (16 hour) | 5 | 2 | 5 | 0 |
| Acetone (10%, 10 h) | 2 | 4 | 4 | 4 |

The results for Examples D6 to D9 show that, upon decreasing the ratio of dimer fatty acid to dicarboxylic acid, the 100% modulus and hardness of the polyurethane dispersion increases. At higher ratios (75:25 in Example D6) the polyurethane dispersion film formation was not optimal, related to large particle size (which preferably is maximum 150 nm). This resulted in increased water uptake.

Polyurethane dispersions were also formed from the polyurethanes of Examples 10 to 13 using the same method as described for Examples D1 to D5. Dispersions D10 to D13 were formed, and various physical properties were measured for each dispersion in the form of a coating.

The test methods used to determine the properties as shown in Table 4 were the same as described with reference to dispersions D1 to D5.

TABLE 4

Evaluation of coatings comprising polyurethane dispersions D10 to D13

|  | D10 | D11 | D12 | D13 |
|---|---|---|---|---|
| Particle size (nm) | 76 | 69 | 117 | 127 |
| König hardness (s) | 33 | 32 | 31 | 37 |
| Water absorption | 6 | 7 | 5 | 6 |
| Chemical resistance to: | | | | |
| NaCl (5%, 5 h) | 0 | 0 | 0 | 0 |
| Water (16 h) | 0 | 0 | 0 | 0 |
| Acetone (10%, 10 h) | 3 | 4 | 4 | 3 |
| Ethanol (50%, 1 h) | 5 | 5 | 5 | 4 |

Examples D11 to D13 show that upon increasing the molecular weight of the dicarboxylic acid, an increase is seen in the hardness as well as in the chemical resistance. Comparing examples D10 and D11, water absorption increases and chemical resistance reduces, moving from hexanediol to butanediol. This is improved by replacing adipic acid with a larger dicarboxylic acid. This improvement can be seen by comparing D12 (sebacic acid) and D13 (dodecanedioic acid) with D11 (adipic acid).

Polyurethane dispersions were also formed from the polyurethanes of Examples 14 and 15 using the same method as described for Examples D1 to D5. Dispersions D14 and D15 were formed, and various physical properties were measured for each dispersion in the form of a coating.

The test methods used to determine the properties as shown in Table 4 were the same as described with reference to dispersions D1 to D5.

TABLE 5

Evaluation of coatings comprising polyurethane dispersions D14 and D15

|  | D14 | D15 |
|---|---|---|
| Particle size (nm) | 179 | 127 |
| König hardness (s) | 34 | 37 |
| Water absorption | 9 | 6 |
| Chemical resistance to: | | |
| NaCl (5%, 5 h) | 0 | 0 |
| Water (16 h) | 3 | 0 |
| Acetone (10%, 10 h) | 3 | 3 |
| Ethanol (50%, 1 h) | 5 | 4 |

Examples D14 and D15 show that upon increasing the ratio of dimer fatty acid to dicarboxylic acid (D14 has 75% dimer fatty acid and D15 has 50% dimer fatty acid), the hardness decreases and the particle size of the polyurethane dispersion (PUD) tends to become higher. Reasonable film formation of the polyurethane dispersion coating was obtained in both D14 and D15. However, the chemical resistance of D14 was reduced, especially to water. The particle size may be reduced by process optimisation, or otherwise by formulation adjustment.

Example D5A

Adhesive Polyurethane Dispersions

Polyurethane dispersions with hydroxyl functionality were made from the polyester. The polyester of Example 5 was used, having a weight ratio of dimer fatty acid and dicarboxylic acid of 50:50. The polyurethane dispersion of Example D5A was synthesised via formation of a pre-polymer, and the components present are shown in Table 6.

TABLE 6

Components for D5A Synthesis

| Amount Used | Component | Function |
|---|---|---|
| 200 g | Polyester | |
| 20 g | 2,2-Dimethoxy-2-phenylacetophenone (DMPA) | |
| 53 g | Isophorone diisocyanate (IPDI) | Polyisocyanate |
| 40 g | N-Methyl-2-pyrrolidone (NMP) | Organic solvent |
| 16.6 g | Triethylamine (TEA) | |
| 360 g | Water | |

The polyester, DMPA and NMP were dried at 120° C. under nitrogen. After cooling to 70° C., dibutyl tin dilaurate (DBTL) catalyst (0.05 wt. % based on the weight of the pre-polymer) and IPDI were slowly added over approximately 3 hours at 75° C. to produce the pre-polymer. Then at 60° C. triethylamine was added to neutralise the DMPA carboxylic acid groups over a period of 0.5 to 1 hour. The reaction mixture was then cooled to 60° C. After cooling, the prepolymer was dispersed in demineralised water which was added slowly over 1 hour under vigorous stirring.

The resultant dispersion comprised 40 wt. % of the polyurethane. Acetone can be used as processing aid to reduce viscosity, and can then be distilled off from the final polyurethane dispersion.

The adhesive polyurethane dispersion (PUD) was applied to the substrate, dried and re-activated at 70° C. A steel weight was used to join the two parts, in lap-shear mode. Adhesive strength was tested on an Instron tensile tester. (lap shear adhesion method ISO 4587). Strong adhesion was found on birch wood, at 5.4 MPa.

Sample D5A (from polyester of Example 5) was compared on a rigid PVC substrate with a polyurethane dispersion with hydroxyl functionality that was made from the comparative polyester Example 1. The Lap shear adhesive strength of D5A was 1.9 MPa compared with 0.8 MPa for the comparative PUD from polyester Example 1.

Example E1 and E5

Polyurethane Elastomers

Polyester of Example 5 was used, made from of 1,3-propanediol, dimer fatty acid, and dodecanedioic acid. The dimer fatty acid and dicarboxylic acid were use at weight ratio of 50:50. This was formed in to an elastomer by the method as described below to yield Example E5.

Comparative polyester based on Example 1 was made from 1,6-hexanediol, dimer fatty acid, and adipic acid. The dimer fatty acid and dicarboxylic acid were use at weight ratio of 50:50. This was formed in to an elastomer by the method as described below to yield Example E1.

The polyurethane elastomers were prepared using 1 part polyester, 2 parts 1,4-butanediol (BDO) as a chain extender, and 3.1 parts 4,4'-diphenylmethane diisocyanate (MDI), using a one-shot method. To form elastomers polyester and 1,4-butanediol (BDO) chain extender were blended and pre-heated at 50° C. and degassed in a degassing chamber. The polyester and BDO were mixed thoroughly, after which molten 4,4'-diphenylmethane di-isocyanate (MDI) was added. The reaction mixture was stirred efficiently, transferred to the degassing chamber for a few minutes until significant viscosity increase occurred. The mixture was then poured into a preheated 100° C. steel mould. The mould was closed and transferred to an oven at 100° C. After 2 hours the elastomer was de-moulded and further cured at 100° C. for another 18 hours.

The physical properties of each elastomer Examples E1 and E5 were determined and were:
E1—Resulting polyurethane elastomer had a hardness of 81 Shore A and a 100% modulus of 65 kg/cm$^2$.
E5—Resulting polyurethane elastomer had a hardness of 83 Shore A and a 100% modulus of 70 kg/cm$^2$.

The resulting elastomer of Example E5 was flexible with good mechanical properties, and demonstrating good polymerisation. It was also demonstrated that the resulting polyurethane elastomers of the same formulation could also be prepared using a pre-polymer or quasi-pre-polymer method, giving proper elastomer sheets.

It is to be understood that the invention is not to be limited to the details of the above embodiments, which are described by way of example only. Many variations are possible.

The invention claimed is:
1. A polyurethane, said polyurethane being the reaction product of a polyisocyanate and polyester, wherein said polyester is formed from a dimer fatty acid derived from the dimerization products of $C_{14}$ to $C_{22}$ fatty acids, a diol selected from propanediol or butanediol, and a $C_{10}$ or $C_{12}$ linear aliphatic dicarboxylic acid, wherein the ratio of the dimer fatty acid derived from the dimerization products of $C_{14}$ to $C_{22}$ fatty acids to the $C_{10}$ to $C_{12}$ linear aliphatic dicarboxylic acid ranges from about 25:75 to about 50:50, wherein the polyester has a molecular weight number average in the range from 800 to 5,000 and wherein a particle size of the polyurethane is 150 nm or less.

2. The polyurethane according to claim 1, wherein the dimer fatty acid is derived from the dimerisation products of oleic acid, linoleic acid, linolenic acid, palmitoleic acid, and/or elaidic acid.

3. The polyurethane according to claim 1, wherein the dimer fatty acid has a dimer fatty acid content of greater than 60 wt.%.

4. The polyurethane according to claim 1, wherein the propanediol or butanediol has a renewable carbon content of at least 50% when determined using ASTM D6866.

5. The polyurethane according to claim 1, wherein the dicarboxylic acid is a non-dimeric dicarboxylic acid.

6. The polyurethane according to claim 1, wherein the dicarboxylic acid is selected from sebacic acid (decanedioic acid), dodecane dicarboxylic acid (dodecanedioic acid), or combinations thereof.

7. The polyurethane according to claim 5, wherein the dicarboxylic acid has a renewable carbon content of at least 50% when determined using ASTM D6866.

8. The polyurethane according to claim 1, wherein the ratio of carbon atoms of propanediol or butanediol to the ratio of carbon atoms in the dicarboxylic acid is in the range from 1:1.5 to 12 respectively.

9. The polyurethane according to claim 1, wherein the polyester is formed from dimer fatty acid; $C_{10}$ or $C_{12}$ linear aliphatic dicarboxylic acids; and 1,3 propanediol or 1,4 butane diol at a weight ratio in the range from 0.3 to 0.5:0.5 to 0.7:1.0 to 3.0 respectively.

10. The polyurethane according to claim 1, wherein the polyester has a glass transition temperature ($T_g$) value in the range from −60° C. to 0° C.

11. A method of forming polyurethane in accordance with claim 1, the method comprising;
forming polyester from a dimer fatty acid derived from the dimerization products of $C_{14}$ to $C_{22}$ fatty acids, a diol selected from propanediol or butanediol, and a $C_{10}$ or $C_{12}$ linear aliphatic dicarboxylic acid, wherein the ratio of the dimer fatty acid derived from the dimerization products of $C_{14}$ to $C_{22}$ fatty acids to the $C_{10}$ to $C_{12}$ linear aliphatic dicarboxylic acid ranges from about 25:75 to about 50:50, wherein the polyester has a molecular weight number average in the range from 800 to 5,000; and
reacting said polyester with a polyisocyanate to form polyurethane having a particle size of 150 nm or less.

12. A method of forming polyurethane in accordance with claim 1, the method comprising;
forming polyester from a dimer fatty acid derived from the dimerization products of $C_{14}$ to $C_{22}$ fatty acids, a diol selected from propanediol or butanediol, and a $C_{10}$ or $C_{12}$ linear aliphatic dicarboxylic acid, wherein the ratio of the dimer fatty acid derived from the dimerization products of $C_{14}$ to $C_{22}$ fatty acids to the $C_{10}$ to $C_{12}$ linear aliphatic dicarboxylic acid ranges from about 25:75 to about 50:50, wherein the polyester has a molecular weight number average in the range from 800 to 5,000; and
reacting said polyester with polyisocyanate to form an isocyanate-terminated prepolymer; and reacting said prepolymer with a chain extender to form a polyurethane having a particle size of 150 nm or less.

13. The method according to claim 11, wherein the polyisocyanate comprises at least one isocyanate which has a functionality of at least 2.

14. The method according to claim 12, wherein the chain extender is a diol having an aliphatic linear carbon chain comprising in the range from 1 to 10 carbon atoms.

15. The method according to claim 12, wherein the molar ratio of chain extender to polyester is in the range from 1 to 10:1.

16. An isocyanate-terminated pre-polymer which is a reaction product of polyisocyanate and polyester, wherein said polyester is formed from a dimer fatty acid derived from the dimerization products of $C_{14}$ to $C_{22}$ fatty acids, a diol selected from propanediol or butanediol, and a $C_{10}$ or $C_{12}$ linear aliphatic dicarboxylic acid, wherein the ratio of the dimer fatty acid derived from the dimerization products of $C_{14}$ to $C_{22}$ fatty acids to the $C_{10}$ to $C_{12}$ linear aliphatic dicarboxylic acid ranges from about 25:75 to about 50:50, wherein the polyester has a molecular weight number average in the range from 800 to 5,000 and wherein the prepolymer has a particle size of 150 nm or less.

17. An adhesive, coating, or elastomer composition comprising polyurethane in accordance with claim 1.

* * * * *